(12) United States Patent
Fischer

(10) Patent No.: US 6,613,523 B2
(45) Date of Patent: Sep. 2, 2003

(54) METHOD OF DNA SEQUENCING USING CLEAVABLE TAGS

(75) Inventor: Steven M. Fischer, Hayward, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/896,299

(22) Filed: Jun. 29, 2001

(65) Prior Publication Data

US 2003/0008285 A1 Jan. 9, 2003

(51) Int. Cl.[7] .................. C12Q 1/68; C12P 19/34; C12P 19/58; C12P 19/56; C07H 21/04
(52) U.S. Cl. .................. 435/6; 435/91.2; 435/77; 435/78; 536/24.33; 536/25.3; 536/27
(58) Field of Search .................. 435/6, 91.2, 77, 435/78; 536/24.33, 25.3, 27

(56) References Cited

U.S. PATENT DOCUMENTS

| | | | |
|---|---|---|---|
| 4,971,903 A | 11/1990 | Hyman | 435/6 |
| 5,302,509 A | 4/1994 | Cheeseman | 435/6 |
| 5,552,278 A * | 9/1996 | Brenner | 435/6 |
| 6,027,890 A | 2/2000 | Ness et al. | 435/6 |
| 2002/0040873 A1 * | 4/2002 | Wahlberg et al. | 210/635 |

FOREIGN PATENT DOCUMENTS

| | | | |
|---|---|---|---|
| WO | WO 98/28440 | 7/1988 | C12Q/1/68 |
| WO | WO 98/13523 | 4/1998 | C12Q/1/68 |
| WO | WO 99/66313 | 12/1999 | C12Q/1/68 |
| WO | WO 00/40750 | 7/2000 | C12Q/1/68 |
| WO | WO 00/43540 | 7/2000 | C12Q/1/16 |
| WO | WO 00/56455 | 9/2000 | |

OTHER PUBLICATIONS

Prober, et al., "A System for Rapid DNA Sequencing with FLuorescent Chain–Terminating DideoxyNucleotides" Science, 238: 336–341, 1987.
Sanger, et al., "DNA Sequencing with Chain–Terminating Inhibitors", Proc. Natl. Acad. SCi. USA, 74(12): 5463–5467, 1977.

* cited by examiner

*Primary Examiner*—Ethan Whisenant
*Assistant Examiner*—Joyce Tung

(57) ABSTRACT

The present invention provides novel systems for sequencing nucleic acid molecules using dNTPs that are 3' end labeled with cleavable tags that block further extension and uniquely identify the bases to which they are attached. Removal of the tags liberates the 3' ends of the extension products for further extension. In related embodiments, oligonucleotides containing sequence-related cleavable tags are employed in a ligation reaction to determine the sequence of a particular DNA sample.

16 Claims, No Drawings

METHOD OF DNA SEQUENCING USING CLEAVABLE TAGS

BACKGROUND OF THE INVENTION

DNA sequencing is an important analytical technique critical to generating genetic information from biological organisms. The increasing availability of rapid and accurate DNA sequencing methods has made possible the determination of the DNA sequences of entire genomes, including the human genome. DNA sequencing has revolutionized the field of molecular biological research. In addition, DNA sequencing has become an important diagnostic tool in the clinic, where the rapid detection of a single DNA base change or a few base changes can be used to detect, for example, a genetic disease or cancer.

Most current methods of DNA sequencing are based on the method of Sanger (*Proc. Natl. Acad. Sci U.S.A.*, 74, 5463 (1977)). This method relies on gel electrophoresis of single stranded nucleic acid fragments that are generated when a polymerization extension reaction of a primer is terminated by incorporation of a radioactively labeled dideoxynucleotide triphosphate. Short strands of DNA are synthesized under conditions that produce DNA fragments of variable length using a DNA polymerase and deoxynucleotide triphosphates (dNTP). A small amount of dideoxynucleotide triphosphates (ddNTP) is introduced into the DNA synthesis mixture so that chain terminating ddNTPs are sometimes integrated into a growing strand. Typically, four different extension reactions are performed side by side, each including a small amount of one ddNTP. Each extension reaction produces a mixture of DNA fragments of different lengths terminated by a known ddNTP. The ratio of ddNTPs to dNTPs is chosen so that the populations of DNA fragments in any given extension reaction includes fragments of all possible lengths (up to some maximum) terminating with the relevant ddNTP. The nucleic acid fragments are separated by length in the gel, typically utilizing a different lane in a polyacrylamide gel for each of the four terminating nucleotide bases being detected. However, such size exclusion chromatography is generally a low resolution method limited to reading short sequences.

A variation of this method utilizes dyes rather than radioactivity to label the ddNTPs. Different dyes are used to uniquely label each of the different ddNTPs (i.e., a different dye may be associated with each of A, G, C, and T termination) (Smith et al. and Prober et al. *Science* 238:336–341, 1987). In the method of Smith, fluorescent dyes are attached to the 3' end of the dNTP converting it into a ddNTP. The use of four different dye labels allows the entire sequencing reaction to be conducted in a single reaction vessel and results in a more uniform signal response for the different DNA fragments. The dye-terminated dNTPs are also able to be electrophoresed in a single lane. The advent of capillary electrophoresis further increased the separation efficiency of this method, allowing shorter run times, longer reads, and higher sensitivity.

Despite these advances, DNA sequencing methods that rely on electrophoresis to resolve DNA fragments according to their size are limited by the rate of the electrophoresis and the number of bases that are detectable on the gel. In addition, real time imaging of the gel is not possible. Accordingly, in order to increase the speed and reliability of the sequencing reaction, great effort has been made to automate these steps. Automated DNA sequencing machines are now available that are capable of high throughput sequencing for both genomic sequencing and routine clinical applications. However, these newer techniques remain cumbersome, requiring specialized chemicals and the intensive labor of skilled technicians.

One newer method of DNA sequencing, "pyrosequencing" or "sequencing-by-synthesis," disclosed in WO 98/13523, is based on the concept of detecting inorganic pyrophosphate (PPi), which is released during a polymerase reaction. As in the Sanger method, a sequencing primer is hybridized to a single stranded DNA template and incubated with a DNA polymerase. In addition to the polymerase, the enzymes ATP sulfurylase, luciferase, and apyrase, and the substrates, adenine 5' phosphosulfate (APS) and luciferin, are added to the reaction. Subsequently, individual nucleotides are added. When the added nucleotide is complementary to the next available base in the template strand, it is incorporated into the extension product. Such incorporation of a complementary base is accompanied by release of pyrophosphate (PPi), which is converted to ATP in the presence of adenosine 5' phorphosulfate by apryase in a quantity equimolar to the amount of incorporated nucleotide. The ATP generated by the reaction with apyrase then drives the luciferase mediated conversion of luciferin to oxyluciferin, generating visible light in amounts that are proportional to the amount of ATP and thus the number of nucleotides incorporated into the growing DNA template. The light produced by the luciferase-catalyzed reaction is detected by a charge coupled device (CCD) camera and detected as a peak in a pyrogram™.

In a pyrosequencing reaction, if the first nucleotide added to the reaction is not complementary to the next available nucleotide on the growing DNA strand there is no light generated. If no light is generated by the addition of the first nucleotide, a second of four dNTPs is added sequentially to the reaction to test whether it is the complementary nucleotide. This process is continued until a complementary nucleotide is added and detected by a positive light read-out. Whether or not a positive light reaction is generated, apyrase, a nucleotide-degrading enzyme, continuously degrades unincorporated dNTPs and excess ATP in the reaction mixture. When degradation is complete, another dNTP is added.

Although pyrosequencing is capable of generating high quality data in a relatively simple fashion, this method has several drawbacks. First, the productivity of the method is not high, reading only about 1 base per 100 seconds. The rate of the reaction is limited by the necessity of having to add new enzymes with each addition of the dNTPs in addition to the necessity of having to test each of the four dNTPs separately. In addition, it has been found that the dATP used in the chain extension reaction interferes in subsequent luciferase-based detection reactions by acting as a substrate for the luciferase enzyme. Finally, these reactions are expensive to run.

While pyrosequencing improves the ease and speed with which DNA sequencing is achieved, there exists the need for improved sequencing methods that allow more rapid detection. Preferred techniques would be amenable to automation and allow the sequence information to be revealed simultaneously with or shortly after the chain extension reaction.

SUMMARY OF THE INVENTION

The present invention provides a novel system for sequencing nucleic acid molecules. In particular, the invention utilizes dNTPs that are 3' end labeled with a cleavable tag that distinguishes the dNTP from other dNTPs (e.g., the tag may be unique to the dNTP). The cleavable tags are functional groups that can be later removed by any appropriate means, including but not limited to, exposure to chemical cleavage conditions or light. dNTPs labeled with the cleavable tags function as terminated dNTPs (cdNTPs), in that their incorporation into a single stranded nucleic acid molecule via a primer extension reaction blocks further extension. However, removal of the tag converts the cdNTP back into an extendible nucleotide.

According to the present methods, a sequencing primer is hybridized to a nucleic acid template, e.g., a single stranded DNA template, and incubated with an enzyme (DNA polymerase) and four cdNTPs (tag terminated dATP (cdATP), dCTP (cdCTP), dGTP (cdGTP), and dTTP (cdTTP)). The DNA polymerase then extends the primer by adding to it whichever cdNTP is complementary to the next available base on the template strand. Only a single cdNTP is incorporated, because the cdNTP cannot be further extended.

After completion of a single base addition, unreacted (excess) cdNTPs are removed from the reaction mixture, which includes the extended primer, the DNA polymerase, and the single stranded DNA template. The step of removing can be accomplished by any of a variety of means that would be apparent to one skilled in the art. For example, if the reaction mixture is contained in a chamber that has an attached membrane (e.g., an ultrafiltration membrane that allows small molecules such as water, salts, and cdNTPs to pass through, but does not allow passage of large molecules such as single stranded DNA), the excess cdNTP can be washed through the membrane. Alternatively, if the single stranded DNA is attached to a solid support, the excess cdNTPs can be washed away from the single stranded DNA without dislodging the hybridized, extended primer.

Once the step of removing is complete, the tag is cleaved from the cdNTP that is extended into the single stranded DNA template. In certain embodiments, the cleavage occurs by photo-cleavage of the tag from the extended single stranded DNA template by exposure to light. Alternatively, in other preferred embodiments, the cleavage occurs by exposure of the single stranded DNA template to a chemical cleaving agent, e.g., an acid or a base. Whichever cleavage method is employed, the result is liberation of the 3' end of the extension product for further extension.

The cleaved tag is then washed through the membrane into a detector for identification, thereby identifying the complementary base in the single stranded DNA template and determining the DNA sequence. The detector used to identify the tag is chosen based on the type of cleavable tag employed. Any of a variety of tags may be employed in the present invention, as would be recognized by the skilled artisan, and such tags are described herein. Once the tag is cleaved, the four cdNTPs are added back to the primer extension reaction mixture and the cycle of extension, tag cleavage, and identification is repeated.

In other preferred embodiments, short oligonucleotides are employed in a ligation reaction to determine the sequence of a particular DNA sample. The sequence of a DNA sample is determined by incorporating "X" complementary bases (e.g., 2 mers, 3 mers, or more) at a time onto the single stranded DNA template adjacent to a primer using a DNA ligase instead of using a DNA polymerase. Each oligonucleotide is tagged and labeled with a cleavable tag so that the position of each base in the sequence of the oligonucleotide can be identified. The tag further prevents ligation of the oligonucleotides to one another.

According to this aspect of the invention, a template DNA is exposed to the oligonucleotides, the oligonucleotides are allowed to hybridize to the template DNA, and a ligation reaction is allowed to take place on the DNA template such that one complementary oligonucleotide is incorporated onto the DNA template adjacent to the annealed primer. Following ligation, the unincorporated oligonucleotides are washed away from the DNA sample and the tags are cleaved and analyzed to determine the nucleic acid sequence.

DETAILED DESCRIPTION OF CERTAIN PREFERRED EMBODIMENTS

The present invention provides a system for sequencing a DNA molecule using deoxynucleotide triphosphates of adenine, thymine, guanine, and cytosine that are each labeled with a different cleavable tag that is used to identify the base. In preferred embodiments, the cleavable tag further acts as a terminator to extension of a single stranded DNA template in a polymerase extension reaction until the tag is removed from the incorporated base. Once removed, the tag is isolated and identified, and the process of base addition and cleavage is repeated. More particularly, the steps of extension, cleavage, and detection are repeated until sufficient sequence of the single stranded DNA template is determined.

According to certain preferred embodiments, inventive methods of determining the sequence of a nucleic acid include the steps of (a) hybridizing an oligonucleotide to a single stranded DNA, wherein the oligonucleotide is complementary to at least a portion of the single stranded DNA; (b) providing a DNA polymerase and four deoxynucleotide triphosphates (dNTPs) (e.g., DATP, dGTP, dCTP, and dTTP) wherein each dNTP is 3' end labeled with a cleavable tag (cdNTP) that distinguishes the dNTP from other dNTPs; (c) extending the single stranded DNA hybridized to the oligonucleotide by adding one complementary cdNTP in a polymerase extension reaction, wherein the tag on the extended cdNTP blocks further extension by the DNA polymerase; (d) optionally removing excess cdNTPs that are not extended onto the single stranded DNA; (e) cleaving the tag from the extended cdNTP; and (f) detecting the tag so that the incorporated base is detected. In certain preferred embodiments, the method includes the step of repeating steps (a) through (f) on the sample of single stranded DNA.

As indicated above, prior to cleavage of the tag from the extended base on the DNA template, the excess, unincorporated cdNTPs are preferably removed from the extension reaction. According to the invention, the tags may be removed by any of a variety of washing or rinsing procedures that separate the excess, unincorporated dNTPs from the extended DNA template. In one preferred embodiment, the extension reaction is contained within a chamber that has an attached filtration membrane, e.g., an untrafiltration membrane, that allows small molecules such as water, salts, and cdNTPs to pass through, while retaining large molecules such as ssDNA. According to this particular embodiment, a wash solution, e.g., a buffered saline solution such as phosphate buffered saline, is passed through the ultrafiltration membrane of the chamber containing the oligonucleotide primer, the DNA polymerase, the cdNTPs, and the extended DNA to rinse away the excess cdNTPs. Alternatively, if the DNA template is attached to a solid support, a wash solution may be passed over the solid support to rinse the excess cdNTPs away from the solid support.

In a related embodiment, the sequencing method of the present invention is also amenable to sequence determination via oligonucleotide ligation. This technique requires first exposing the DNA template to a collection of tagged oligonucleotides (e.g., the tagged oligonucleotides may be a collection of short randomized oligonucleotides). Preferably, a 3' tag blocks further litgation at the 3' end of the oligonucleotide to other oligonucleotides in the collection. However, it will be appreciated that if the tag is located at a position on the oligonucleotide other than the 3' end, the 3' end of the oligonucleotide would still need to be blocked, for example, with another functional group. Once the DNA template is mixed with the tagged oligonucleotides, the oligonucleotides are allowed to hybridize to the DNA template in a position adjacent to an oligonucleotide primer so that the oligonucleotide and primer can be ligated. Unligated oligonucleotides are then rinsed away from the DNA template, tags are cleaved from the ligated oligonucleotides, and cleaved tags representing the bases of the ligated oligonucleotide are detected. This cycle can be repeated as described, with addition of the oligonucleotide mix occurring at each repetition.

In certain preferred embodiments, the number of tags attached to the 3' end of the oligonucleotide may be based on the sequence length of the oligonucleotide. For example, an oligonucleotide that is three bases long may be 3' end labeled with three tags that are attached in a sequential order matching the sequential order of the bases of the oligonucleotide.

In the oligonucleotide ligation reaction, as with the polymerase reaction, the DNA template is a single stranded DNA template that is annealed to a primer for primer extension. By "single stranded DNA template" is meant any single stranded DNA template or single stranded DNA template that is partially single stranded, i.e., may be partially double stranded. In one preferred embodiment, an oligonucleotide that is 3' end blocked and complementary to the sequence adjacent to the primer anneals to the DNA template and is joined to the adjacent primer via a ligase (e.g., T4 DNA ligase). The tags on the complementary oligonucleotide are then removed for detection and identification, freeing the 3' end of the complementary oligonucleotide for subsequent rounds of ligation. In such subsequent rounds, the ligase joins the next complementary blocked oligonucleotide to the 3' end of the previously extended primer and the cycle repeats.

As mentioned above, the collection of oligonucleotides may include short randomized oligonucleotides. Those skilled in the art will appreciate that the longer the oligonucleotide, the greater the number of oligonucleotides will have to be generated to encompass all possible random oligonucleotide sequences, based on randomization between four bases at each position of the oligonucleotide. For example, generation of a collection of 2 mers that encompasses all possible 2 mers would require sixteen oligonucleotide sequences; generation of a collection of 3 mers that encompasses all possible 3 mers would require a panel of 64 oligonucleotide sequences; 4 mers would require a panel of 256 oligonucleotide sequences, etc. Identification of an optimal oligonucleotide length may require simply testing various short random oligonucleotide mixes and determining which give the most rapid and accurate DNA sequencing results via oligonucleotide ligation. Of course, the longer the oligonucleotide, the faster the sequencing reaction will proceed, due to the increased number of incorporated bases detected simultaneously. Using this approach, at each round of the sequencing reaction, the oligonucleotide sequence that is ligated to the primer is detected and identified.

In certain preferred embodiments, it is conceivable that only a small subset of all possible oligonucleotides need to be used in the sequencing reaction, for example, if the sequence of the DNA template were partially determined (i.e., if certain positions of the oligonucleotide were fixed, fewer base positions would need to be randomized, limiting the number of oligonucleotide required to include all possible permutations). In this particular embodiment, the oligonucleotides could be longer (e.g., 5 mer, 6 mers, 7 mers, 8 mers, 9 mers, 10 mers, or greater than 15 mers, 20 mers, 25 mers, 30 mers and higher). It is also possible that in certain circumstances one would not need to use as many tags i.e., one would not need to use one tag for every base. For example, one unique tag could be used to identify an entire oligonucleotide sequence.

In other preferred embodiments, two or more unique tags could be used to identify an entire oligonucleotide sequence, the total number of tags being less than the total number of bases in the oligonucleotides (e.g., each tag could identify short sequential stretches of oligonucleotides (e.g., a 3 mer or a 4 mer etc.) within the entire oligonucleotide sequence). In a related embodiment, an oligonucleotide, particularly an oligonucleotide used in the ligation aspect of the invention, may not be randomized at every position (e.g., if certain nucleotide positions are fixed), and may even be randomized at only one or several positions, e.g., 1-2, 1-3, 1-4 or 1-5 positions. Under these circumstances, only a subset of possible variations would be relevant.

In embodiments where the length of the oligonucleotide sequence increases the number of tags required to identify the oligonucleotide sequence, the availability of many unique mass tags makes mass spectrometry a particularly useful system for detection. Since each short random oligonucleotide must be labeled with a unique tags, the short random oligonucleotide may have a maximum length in certain circumstance (e.g., the length and number of oligonucleotides in a collection of oligonucleotides may be limited by the availability of different unique tags). However, mass tags may have the same nominal mass and vary in structure, thereby increasing the diversity of tags available.

Although the level of diversity available in the mass spectrometry system is sufficient to permit unique MS/MS fragmentation, those skilled in the art will appreciate that, because identification of the incorporated oligonucleotides is based on the MS/MS parent/daughter transition, if an MS/MS approach is used, multiplexing target DNA samples is not possible. The MS/MS approach requires the isolation of a single mass followed by fragmentation and mass analysis. Multiplexing would present too many masses for isolation and fragmentation to be practical. However, the MS/MS approach would be helpful in increasing the potential number of mass tags required for coding the oligonucleotides used in the ligation reaction.

Thus, according to the oligonucleotide ligation aspect of the invention, the sequence of a single stranded DNA template may be determined by (a) hybridizing a complementary oligonucleotide to a single stranded DNA adjacent to a primer, wherein the oligonucleotide is 3' end labeled with one or more cleavable tags unique to the oligonucleotide sequence; (b) ligating the hybridized complementary oligonucleotide to the primer, wherein the one or more tags on the extended cdNTP blocks further ligation by the DNA ligase; (c) optionally removing excess oligonucleotides that are not ligated; (d) cleaving the one or more tags from the ligated complementary oligonucleotide; (e) detecting the one or more tags. In certain preferred embodiments, steps (a) through (e) are repeated on the single stranded DNA.

As in the polymerase reaction, in the ligation reaction, prior to cleavage of the tag(s) from the extended oligonucleotide on the DNA template, the excess oligonucleotides are preferably removed. The oligonucleotides may be removed by any of a variety of separation procedures that may include washing or rinsing the unincorporated oligonucleotides away from the extended DNA template. As with the polymerase reaction, in one preferred embodiment, the ligation reaction is contained within a chamber that has an attached filtration membrane that would allow short oligonucleotides to pass through, while retaining larger molecules, such as the DNA template. Alternatively, the DNA template is attached to a solid support and a wash solution may be passed over the solid support to remove the unincorporated tagged oligonucleotides.

As will be appreciated by those skilled in the art, whether the sequencing reaction employs a DNA polymerase or a DNA ligase, any tag that is cleavable by chemical means or by light can be used in the present invention. In certain preferred embodiments, the tag is cleaved by exposure to an acid or a base. In other preferred embodiments, the tag is cleaved by exposure to light, i.e., in a photo-cleavage reaction. The cleavable tags themselves include any functional group that imparts a unique identity onto the oligonucleotide or base that is tagged. According to the present invention, useful tags include, e.g., fluorescent tags, mass tags, IR tags, UV tags, potentiometric tags, etc. For example, a fluorescent tag may be attached to a dNTP prior to the primer extension reaction, and then may be cleaved from the dNTP after the dNTP is incorporated into the extended DNA strand by exposure of the extended DNA strand to an acid, a base, or light, and analyzed using fluorescence spectrometry. As but another example, a base having an acid, base, or light cleavable mass tag, after incorporation into the DNA template, may be cleaved from the extended DNA strand using the appropriate cleavable agent, and then may be analyzed using mass spectrometry.

The DNA sequencing methods of the present invention provide an advantage over existing Sanger-based methods by eliminating the need to separate cDNA fragments on a gel, resulting in longer sequence reads. The present method is rapid and fully automatable. In addition, the selection and detection of one of the four bases is carried out simultaneously.

Alternatively, the identification step need not be carried out simultaneously with the cycling of the reaction. For example, the tags from each cycle may be collected and pooled (e.g., onto a 96 well plate). Alternatively, the tags from each cycle may be spatially arrayed (e.g., onto a chip) and the positional information used for identification. Using either method, the tags are analyzed subsequent to the cycling reaction by art available means. Such collection and analysis may increase the speed of the sequencing reaction to increase the throughput of the technique. Of course one skilled in the art would recognize that the appropriate instrumentation is required to analyze the collected tags.

Certain aspects of the present invention are described in further detail below.

Nucleic Acid Preparation

In certain preferred embodiments of the invention, the DNA sample is a single stranded DNA template. Alternatively, if in a polymerase extension reaction a thermostable DNA polymerase enzyme is employed, the DNA sample may be double stranded.

The DNA sample of the invention may be provided from any available source of DNA, including, for example, a biological sample, including not only samples obtained from living organisms (e.g., mammals, fish, bacteria, parasites, viruses, fungi, and the like) or from the environment (e.g., air water, or solid samples), but biological materials which may be artificially or synthetically produced (e.g., phage libraries, organic molecule libraries, pools of genomic clones, and the like). Representative examples of biological samples include biological fluids (e.g., blood, semen, cerebral spinal fluid, urine), biological cells (e.g., stem cells, B or T cells, fibroblasts, and the like), and biological tissues. Alternatively, the DNA may be a cDNA synthesized from an RNA sample (e.g., from a natural or synthetic source). Such cDNA synthesis may be carried out using reverse transcription, and such systems are readily available.

The DNA sample, whether from a biological or synthetic source, may further be amplified, particularly if the amount of sample DNA is small. Amplification can be carried out by any art available method, for example, in vitro by PCR or Self Sustained Sequence Replication (3 SR) or in vivo using a vector. Alternatively, if desired, in vitro and in vivo amplification may be used in combination (see, e.g., McPherson, "PCR: A Practical Approach," Oxford University Press, New York, 1991). Within other embodiments of the invention, the DNA samples of the present invention may be generated by, for example, a ligation or cleavage reaction.

According to the invention, the DNA sample, amplified or unamplified, is either immobilized on a solid support or in solution. In the case of an amplified DNA sample, those skilled in the art will recognize that any amplification procedure may be modified to allow for attachment of the amplified DNA sample to a solid support. For example, a chosen PCR primer may be immobilized to a solid support or may be provided with a means for attachment to a solid support. Immobilization may take place as part of a PCR amplification, e.g., where one or more primers is attached to a support. Alternatively, one or more primers may carry a functional group, e.g., a biotin or thiol group, permitting subsequent immobilization of the DNA sample. Immobilization of the 5' end of a DNA in the sample, e.g., via a 5' primer, allows the DNA to be attached to a solid support, leaving its 3' end remote from the support and available for subsequent hybridization with the extension primer and extension by the polymerase (or ligase). Alternatively, an unamplified DNA sample, such as a vector or a biological sample, may include, or be modified to include, a functional group that allows attachment to a solid support. In a related embodiment, the vector may include a means for attachment to a solid support adjacent to the site of insertion of the sample DNA such that the amplified DNA sample and the means for attachment may be excised together.

The solid support may conveniently take the form of, for example, microtiter wells, a solid support activated with polystyrene to bind the DNA sample (e.g., primer DNA), particles, beads (e.g., nylon beads, polystyrene microbeads, or glass beads) (Polysciences, Warrington, Pa.), glass surfaces, plates, dishes, flasks (Corning Glass Works, Corning, N.Y.), meshes (Bectom Dickinson, Mountain View, Calif.), membranes (Millipore Corp., Bedford, Mass.), dipsticks, capillaries, hollow fibers (Amicon Corporation, Danvers, Mass.), screens and solid fibers (Edelman et al., U.S. Pat. No. 3,843,324; see also Kuroda et. al., U.S. Pat. No. 4,416,777, incorporated herein by reference), or needles, made, for example, of agarose, cellulose, alginate, Teflon, or polystyrene. Magnetic particles, e.g., majestic beads, may also be used as solid supports, and such materials are commercially available (Robbin Scientific, Mountain View, Calif.).

The solid support may alternatively or additionally carry functional groups such as hydroxyl, carboxyl, aldehyde, or amino groups, or other moieties, such as avidin or streptavidin, for the attachment of the appropriately modified DNA, e.g., via modified oligonucleotide primers used in an amplification reaction. These may in general be provided by treating the support to provide a surface coating of a polymer carrying one of such functional groups, e.g., polyurethane together with a polyglycol to provide hydroxyl groups, or a cellulose derivative to provide hydroxyl groups, a polymer or copolymer of acrylic acid or methacrylic acid to provide carboxyl groups, or an aminoalkylated polymer to provide amino groups. Various other supports and methods of attachment and detachment of nucleic acid molecules to supports, with and without the use of a linker, is described in U.S. Pat. No. 5,789,172, incorporated herein by reference.

As indicated above, the DNA sample need not be attached to a solid support. For example, a polymerase extension reaction may be carried out in solution on a DNA sample that is prepared in the context of a primer extension reaction having a buffer that will accommodate the addition of an oligonucleotide primer, a DNA polymerase, cdNTPs, and a single or double-stranded DNA template. A ligation extension reaction may be similarly carried out in an appropriate buffer in the presence of an oligonucleotide primer, a DNA ligase, tagged oligonucleotide, and a single or double-stranded DNA template.

Extension

Once a suitable DNA sample is prepared, the sample is subject to a primer extension reaction by addition of an oligonucleotide primer, a DNA polymerase, and four cdNTPs, such that one base is incorporated onto the DNA template before extension is blocked by the cleavable tag on the incorporated base. Alternatively, an oligonucleotide ligation reaction is used to extend the template DNA sample, as described above. Those skilled in the art will appreciate that such extension reactions can be modified to accommodate variations in template DNAs, reaction conditions, etc. It will be further recognized that the chosen oligonucleotide primer must be sufficiently large to provide appropriate hybridization with the target DNA sequence. Moreover, the oligonucleotide primer preferably hybridizes immediately 5' to the target sequence. Guidance for selection of primers and primer extension reactions can be found in the scientific literature, for example, Maniatis et al., *Molecular Cloning, a laboratory Manual* (1989).

The polymerase in the primer extension reaction may be any polymerase that incorporates dNTPs, and preferably cdNTPs, onto a single stranded DNA template. Examples of suitable polymerases that may conveniently be used, and many are known in the art and reported in the literature, include T7 polymerase, Klenow, and Sequenase. Those skilled in the art will be aware that certain polymerases, e.g., T7 polymerase, recognize a specific leader sequence in the DNA, which can be included in the sequence of the oligonucleotide primer. If a double stranded DNA template is to be used in the polymerase extension reaction, it is desirable that a thermostable polymerase, such as a Taq polymerase, be chosen to permit repeated temperature cycling without having to add additional polymerase for each round of extension.

It is well known that many polymerases have a proof-reading or error checking ability, which sometimes results in digestion of 3' ends available for extension. In the method of the invention, such digestion may result in an increased level of background noise. In order to avoid this problem, a non-proof-reading polymerase, e.g., an exonuclease deficient (exo-) Klenow polymerase may be used. Otherwise, fluoride ions or nucleotide monophosphates that suppress 3' digestion by the polymerase may be added to the extension reaction mixture. In addition, it may be advantageous to use an excess amount of polymerase over primer/template to maximize the number of free 3' ends that are extended. Those skilled in the art will appreciate that the precise reaction conditions and concentrations of reactants etc. may readily be determined for each system according to choice.

Since the primer is extended by a single base (or a single oligonucleotide) by the methods described above, the extended primer serves in exactly the same way in the repeated procedure, and with each subsequence base (or oligonucleotide) addition, to determine the next base or bases in the sequence, permitting the whole sample to be sequenced.

Separation

In the case of the polymerase extension reaction, prior to cleavage of the tag from the extended DNA template, the excess cdNTPs must be removed from the reaction mixture to prevent contamination of the cleavage product with signals from other unincorporated bases. As mentioned above, this separation may be accomplished by washing the cdNTPs through a membrane filter that allows flow through of small molecules such as water, salts, and cdNTPS, but does not allow the flow through of larger molecules such as the polymerase and the DNA template.

In the case of the ligase extension reaction, prior to cleavage of the tag from the oligonucleotide on the extended DNA template, the unincorporated tagged oligonucleotide must be removed from the reaction mixture to prevent contamination of the cleavage product with signals from the unincorporated tagged oligonucleotides. Depending on whether the DNA template is free in solution or attached to a solid support, the excess unincorporated tagged oligonucleotide may be removed by either filtration or washing the solid support, respectively. Those skilled in the art will appreciate that if the DNA ligase is removed from the extension reaction mixture along with the tagged oligonucleotide, the ligase will need to be added back to the extension reaction mixture in subsequent rounds. This, of course, is also applicable to a sequencing reaction that utilizes a polymerase, where the polymerase is removed from the extension reaction in a separate step with the cdNTPs.

Those skilled in the art will further appreciate that a wide variety of membrane filters are available in the art. For example, molecular filtration, also known as ultrafiltration, is a membrane separation technique used to segregate substances according to molecular weight and size. Molecular filtration is ideally suited to separate salts and other low molecular weight solutes from high molecular weight species. Molecular filtration is based on a pressure differential across the semipermeable membrane to drive permeable materials through the membrane. For this reason, molecular filtration typically separates solutes and concentrates retained materials more rapidly. Molecular filtration membranes appropriate for use in the present invention may be purchased from Millipore Corp., Bedford, Mass.

In another preferred embodiment, a flow through cell is used for single stranded DNA analysis. In this embodiment, the tag is washed away and is sent to the detector directly. One example of a variation on the flow through cell approach that would be amenable to multiplexing is to use a 96 well plate with an ultrafiltration membrane incorporated in the well. The excess reagents are either washed through by pressure or centrifuged through. The tag is then subsequently cleaved from extended nucleotide base, washed through the membrane, and collected for analysis by the method appropriate for the type of tag to be identified. In certain preferred embodiments, the different wells are pooled and the tags analyzed simultaneously to provide greater sample multiplexing as well as throughput.

Where the DNA template is immobilized on a solid support, the separation is accomplished by simply washing the cdNTPs (or tagged oligonucleotide) away from the solid support. For example, one basic approach to retaining the DNA for analysis would be to absorb the target DNA to an adsorptive surface instead of trapping it behind an ultrafiltration membrane. The excess reagents are washed away from the absorbed DNA by rinsing the absorptive surface with a wash solution. The solvents used in the wash step must be chosen to avoid loss of the DNA during the wash steps.

The basic concept of using a membrane to permit flow of the excess reagent away from the DNA in the wash step can be further combined with the concept of adsorbing the DNA to a surface by incorporating a membrane onto a microfluidic chip. Solvent addition, or washes, may be carried out by the use of electro-osmotic flow. In this particular embodiment, all of the reactions and sample pooling occurs on the chip, permitting high throughput at a lower cost compared to the well plate approach. Within further embodiments, the steps of removing, cleaving, and detecting may be performed in a continuous manner (e.g., as a continuous flow), for example, on a single device which may be automated.

Cleavable Tags and Detection

A "tag," according to the present invention, is a chemical moiety that is used to uniquely identify a nucleic acid molecule. In certain preferred embodiments, the nucleic acid molecule is a nucleotide base. In other preferred embodiments, the nucleic acid molecule is a nucleic acid fragment, such as a DNA or an RNA. "Tag" more specifically refers to the tag variable component as well as whatever may be bonded most closely to it.

The tags of the present invention further possess one or more of certain characteristic attributes. The tag is preferably distinguishable from all other tags, particularly from other tags used in a particular reaction. The discrimination from other chemical moieties can be based on the chromatographic behavior of the tag (particularly after the cleavage reaction), its spectroscopic or potentiometric properties, or some combination thereof. In addition, the tag is capable of being detected when present at $10^{-22}$ to $10^{-6}$ mole. The tag is further attachable to the nucleic acid molecule, e.g., nucleotide base or oligonucleotide, through a "chemical handle" (see U.S. Pat. No. 6,027,890, incorporated herein by reference) which may attach the tag to the nucleic acid molecule either directly, or through a linker group. In certain preferred embodiments, the tags block primer extension. The tags are further stable toward all manipulations to which they are subjected, including attachment to the nucleic acid molecule and cleavage from the nucleic acid molecule, and any manipulations of the nucleic acid molecule while the tag is attached to it; nor does the tag significantly interfere with the manipulations performed (e.g., hybridization or enzymatic reactions) on the nucleic acid molecule while the tag is attached to it.

The tags of the present invention include any tag that is cleavable by chemical means or by light, and such tags are discussed in detail below. Chemically cleavable tags include tags that are cleavable by an acid or a base. Photo-cleavable tags include tags that are cleavable by a wavelength of light. Other methods of cleavage include oxidation, reduction, enzymatic, electrochemical, heat, and the like.

As mentioned above, the tag is further capable of terminating a primer extension reaction. In certain preferred embodiments, the terminating nature of the tag may be due to the nature of the tag itself, for example the structure of the tag, e.g., a tag that is sufficiently bulky in its structure so that that it prevents addition of any additional bases to the extension product. Alternatively or additionally, the terminating nature of the tag may be due to the placement of the tag on the base. Preferably, the tag is attached to the base so that when the base is added to the growing 3' end of the extension product the tag effectively blocks the extension of the 3' end by additional bases, once a tagged base has been added. One such example of a tagged base, wherein the tag is attached directly to the base, that would block extension is shown below.

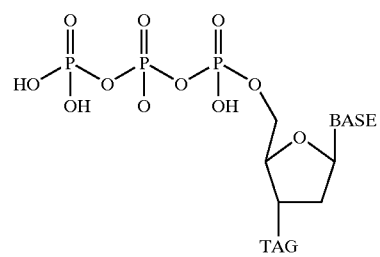

Alternatively, the tag is linked via a labile bond (or labile bonds) to the 3' position of the dNTP, as shown below,

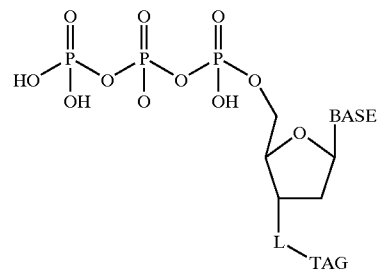

wherein:

L is the linker.

According to the invention, the tag, including the linker in cases where a linker is employed, or other 3' blocking group, are removed to expose the 3' hydroxyl group of the base. Exemplary tags and linkers are described in detail in U.S. Pat. No. 6,027,890, incorporated herein by reference.

In light of the availability of numerous tags, any number of tags may be utilized in a given reaction simultaneously, or within different reactions in an array. In certain preferred embodiments, particularly with respect to detection of ligation products, as described below, 4, 5, 10, 15, 20, 25, 30, 35, 40, 45, 50, 60, 70, 80, 90, 100, 150, 200, 250, 300, 350, 400, 450, or greater than 500 different and unique tagged molecules may be utilized within a given reaction simultaneously, wherein each tag is unique for a selected base, oligonucleotide, or other nucleic acid fragment.

The characteristics of a variety of well known tags that are amenable to attachment to the bases and nucleic acid molecules of the invention are described in U.S. Pat. No. 6,027,890, incorporated herein by reference. Such tags are detectable, once cleaved from the extended base, by fluorometry, mass spectrometry (MS), infrared (IR)

spectrometry, ultraviolet (UV) spectrometry, or potentiostatic amperometry (e.g., utilizing coulometric or amperometric detectors). Mass spectrometry is particularly amendable to multiplexing with mass detection. Representative examples of suitable mass spectrometric techniques include time-of-flight mass spectrometry, quadrupole mass spectrometry, magnetic sector mass spectrometry, and electric sector mass spectrometry. Specific embodiments of such techniques include ion-trap mass spectrometry, electrospray ionization mass specrometry, ion-spray mass spectrometry, liquid ionization mass spectrometry, atmospheric pressure ionization mass spectrometry, electron ionization mass spectrometry, fast atom bombard ionization mass spectrometry, MALDI mass spectrometry, photoionization time-of-flight mass spectrometry, laser droplet mass spectrometry, MALDI-TOF mass spectrometry, APCI mass spectrometry, nano-spray mass specrometry, nebulised spray ionization mass spectrometry, chemical ionization mass spectrometry, resonance ionization mass spectrometry, secondary ionization mass spectrometry, and thermospray mass spectrometry.

The following is a list of representative vendors for separation and detection technologies that may be used in the present invention. Perkin Elmer/Applied Biosystems Division (ABI, Foster City, Calif.) manufacturers semi-automated sequencers based on fluorescent-dyes (ABI373) and (ABI377). Analytical Spectral Devices (Boulder, Colo.) manufactures UV spectrometers. Hitachi Instruments (Tokyo, Japan) manufactures Atomic Absorption spectrometers, Fluorescence spectrometers, LC and GC Mass Spectrometers, NMR spectrometers, and UV-VIS Spectrometers. Perseptive Biosystems (Framingham, Mass.) produces Mass Spectrometers (Voyager™ Elite). Bruker Instruments Inc. (Manning Park, Mass.) manufactures FTIR Spectrometers (Vector 22), FT-Raman Spectrometers, Time of Flight Mass Spectrometers (Reflex II™), Ion Trap Mass Spectrometer (Esquire™) and a MALDI Mass Spectrometer. Analytical Technology Inc. (ATI, Boston, Mass.) makes UV detectors and Diode Array Detectors. Teledyne Electronic Technologies (Mountain View, Calif.) manufactures an Ion Trap Mass Spectrometer 3DQ Discovery™ and the 3dQ Apogee™). Perkin Elmer/Applied Biosystems Division, (Foster City, Calif.) manufactures a Sciex Mass Spectrometer (triple quadrupole LC/MS/MS, the API 100/300), which is compatible with electrospray. Hewlett-Packard (Santa Clara, Calif.) produces Mass Selective Detectors (HP 5972A), MALDI-TOF Mass Spectrometers (HP G2025A), Diode Array Detectors, CE units, HPLC units (HP1090), as well as UV Spectrometers. Finnigan Corporation (San Jose, Calif.) manufactures mass Spectrometers (magnetic sector and four other related mass spectrometers). Rainin (Emeryville, Calif.) manufactures HPLC instruments.

Those skilled in the art will recognize how to apply such devices to the methods of the present invention. Those skilled in the art will further appreciate that devices used to detect pyrosequencing reactions may be adapted to detect and identify the cleaved tags of the invention. For example, the reaction monitoring system described in WO 99/66131, the microfluidic device described in WO 00/40750, the liquid dispensing apparatus described in WO 00/56455, the solid support apparatus of U.S. Pat. No. 5,302,509, each of which is incorporated herein by reference, may be adopted for use with the method of the present invention.

Automation and High-Throughput Sequencing

The DNA sequencing methods of the present invention are fully automatable. Those skilled in the art will recognize that the use of a robot apparatus, where a large number of samples may be rapidly analyzed, may be used for rapid detection and quantification of the tag molecules. Tags to be detected spectrophotometrically may be detected, e.g., by mass spectrometry or fluorescence spectrometry. The use of luminometers, mass spectrometers, and other spectrophotometric devices are well known in the art and described in the literature. The DNA sequencing method of the present invention thus provides an automated approach for high-throughput, non-electrophoretic sequencing procedures that allows for continuous measurement of the progress of the polymerization reaction in real time.

In related embodiments, it will be appreciated that multiple samples may be handled in parallel and such parallel handling provides another advantage to the inventive method. In order to obtain high throughput sequence readout, multiple DNA sequencing reactions can be processed in parallel. According to this particular embodiment, the DNA sequencing method of the present invention can be carried out in any of a variety of array formats.

For example, a single sequencing reaction of the invention, carried out in a single well and analyzed using flow injection analysis (FIA) has a rate of about one base every six seconds (equivalent to about ten bases per minute and about 600 bases per hour). In order to increase this rate, the DNA sequencing reactions may be multiplexed. For example, multiplexing 25 sequences increases the rate of sequencing to about 15000 bases per hour. Those skilled in the art will recognize the power of multiplexing as it is applicable to any means of detection described herein. The number of DNA samples that can be multiplexed for parallel analysis can range 10 to 100, in some cases 100–500, and in yet some other cases, 100–1000 or more DNA samples.

In certain preferred embodiments, an array format is used for analysis wherein the DNA samples are distributed over a surface, for example, a microfabricated chip, thereby immobilizing an ordered set of samples in a 2-dimensional format. This allows the analysis of many samples in parallel. According to this embodiment of the invention, the DNA samples are arrayed onto any of a variety available microchips prior to commencing the sequencing reaction. Methods of producing and analyzing DNA arrays are well known in the art and are provided in U.S. Pat. No. 6,027,789, incorporated herein by reference.

For example, applying the method of the invention to the array format, after primer extension, the tags may be cleaved from the DNA samples on the chip and pooled for analysis using spectrometric or potentiometric techniques (e.g., MALDI-MS). In one particular embodiment of the present invention, an array interrogation system is provided that includes a DNA array generating device, a washing device, a tag cleaving device, a detecting device, and a data processor and analyzer that analyzes data from the detecting device to correlate a tag with a nucleic acid fragment from a sample, as described in U.S. Pat. No. 6,027,789, incorporated herein by reference. The arrayed DNA chip has on its surface selected DNA samples of nucleic acid fragments and cleavable tags, e.g., cleavable mass spectrometer tags, attached to the nucleic acid fragments. The arranged DNA chip is passed through or past a photolytic cleavage device that cleaves the tags from the nucleic acid fragments while still on the DNA chip.

After the tags are cleaved, the DNA chip is positioned in an automated micro-array sampling laser device, such as a Matrix Assisted Laser Desorption Ionization (MALDI) instrument. The MALDI instrument is adapted to irradiate and cause desorption of the tags, which are transferred to a detection device, such as a mass spectrometer, wherein tags are identified based upon the difference in molecular weight.

Data from the detection device is provided to the data processor and analyzer, which includes a software program that maps the signature of a given tag to a specific sample. The software is able to display the DNA sequence determined and load the sequence information into respective data bases.

In an alternative embodiment, the MALDI instrument includes an additional light source that is capable of irradiating the entire DNA chip at a wavelength in the range of 250–360 nm with adjustable intensity, so as to cause the photolytic cleaving of the tags. Accordingly, the cleaving device is incorporated as a component of the MALDI instrument. After cleaving the tags, the MALDI instrument volatized the tags, which are transferred to the detecting device as discussed above.

In yet another embodiment, the DNA chip is moved from the DNA array generating device directly to the MALDI instrument. The MALDI instrument includes a laser that emits at a wavelength in the range of approximately 250 to 360 nm, inclusive. The laser causes the simultaneous photolytic cleavage of the tag from the nucleic acid fragment along with simultaneous desorption of the tag. The tags are then transferred to the mass spectrometer or other detection device, as discussed above. Accordingly, this alternate embodiment provides photocleavage by the MALDI instrument, so that a separate cleavage device is not needed.

If fluorescence sensing is employed in the present invention for detection of the tag, this increases the rate of the sequencing to one base every fifteen seconds (equivalent to about four bases per minute). If 100 sequencing reactions are arranged onto 100 lanes of the chip this yields a rate of about 24000 bases per hour. Similar sequencing rates are achievable with varying cleavage means.

Florescent tags can be identified and quantitated most directly by their absorption and fluorescence emission wavelengths and intensities. While a conventional spectrofluorometer is extremely flexible, providing continuous ranges of excitation and emission wavelengths ($I_{EX}$, $I_{S1}$, $I_{S2}$), more specialized instruments, such as flow cytometers and laser-scanning microscopes require probes that are excitable at a single fixed wavelength. In contemporary instruments, this is usually the 488-nm line or the argon laser.

Radioactive tags may also be applicable to the present invention. Radioactive tags may be detected by, e.g., a CCD detector.

In using fluorescent and radioactive tags, the number of different reactions that are simultaneously detectable may be more limited than, e.g., mass tags. For example, the use of four fluorescent molecules, such as commonly employed in DNA sequence analysis, limits analysis to four samples at a time.

In certain preferred embodiments, the sample reactions may be pooled on at least one array and the products detected simultaneously. By using a cleavable tag, such as the ones described herein, having a different molecular weight or other physical attribute in each reaction, the entire set of reaction products can be harvested together and analyzed.

Applications

The invention in the above embodiments provides a simple and rapid method for sequencing a DNA sample. The methods of the invention both avoid the requirement of separation of the extension product and allows rapid, real-time analysis of the extension reaction. These methods have many applications, which will readily be appreciated by the skilled artisan.

To name but a few, the present invention is applicable in the field of forensics (e.g., the identification of individuals and the level of DNA sequence variations); tumor diagnosis (e.g., for detection of viral or cellular oncogenes in a biological sample from a patient); transplantation analyses (e.g., the identification of antigen specific variable DNA sequences from a biological sample); diagnosis of autoimmune diseases, such as juvenile diabetes, arteriosclerosis, multiple sclerosis, rheumatoid arthritis, and encephalomyelitis; genome diagnostics (e.g., the identification of genetic defects or hereditary and acquired genetic diseases in newborns and adults, for example, schizophrenia, manic depression, epilepsy, sickle-cell anemia, thalessemias, al-antitrypsin deficiency, Lesch-Nyhan syndrome, cystic fibrosis, Duchenn/Becker muscular deficiency, Alzheimer's disease, X-chromosome-dependent mental deficiency, and Huntingtins chorea); infectious disease (e.g. detection of viral or microbial infection of a biological sample); mutation detection (e.g., detection of a mutated base in a DNA sample from a biological or artificial source); detection of single nucleotide changes (e.g., a primer hybridizes to a sequence adjacent to a known single nucleotide polymorphism and a cdNTP added to the adjacent position is detected and identified).

As mentioned above, the method of the present invention may be adapted for use with a ligase instead of a polymerase. One adaptation of this technique is to the oligonucleotide ligation assay, which is used to identify known sequences in very large and complex genomes. To elaborate briefly on the ligase extension reactions described above, the basis of this assay is the ability of a ligase to covalently join two diagnostic oligonucleotides as they hybridize adjacent to one another on a given DNA target. If the sequences at the probe junctions are not perfectly base-paired, the probes will not be joined by the ligase. When tags are used, they are attached to the oligonucleotide, which is ligated to the DNA sample. After a ligation is complete, the tag is cleaved and detected by any of the means described herein (e.g., mass specrometry, infrared spectrophotometry, potentiostatic amperometry, or UV/visible spectrophotometry).

In certain preferred embodiment, the DNA sample is amplified prior to exposure to the oligonucleotide ligation assay.

Kits

The present invention further provides kits for use in methods of the invention that contain at least the following reagents: a) an oligonucleotide primer suitable for primer extension of a particular DNA template; b) four cdNTPs of adenine, guanine, thymine, and cytosine bases; c) a polymerase; d) a separation means to separate unincorporated dNTPS from the extended DNA template; and e) a cleavage means. In certain embodiments of the invention, a detection means will be provided. However, the detection means may often be provided by the purchaser.

In alternative embodiments, if the kit is used for a ligation sequencing reaction assay it may contain at least a) an oligonucleotide primer suitable for primer extension of a particular DNA template; b) at least one tagged oligonucleotide; c) a ligase; d) a separation means to separate unincorporated oligonucleotides from the extended DNA template; and e) a cleavage means. The kit may further provide a detection means. However, the detection means may also be provided by the purchaser.

Other embodiments of the invention will be apparent to those skilled in the art from a consideration of the specification or practice of the invention disclosed herein. It is intended that the specification be considered as exemplary only, with the true scope and spirit of the invention being indicated by the following claims.

What is claimed is:

1. A method of determining a nucleic acid sequence, comprising:
   (a) hybridizing an oligonucleotide to a single stranded DNA within a chamber, wherein a filtration membrane is attached to the chamber, wherein the oligonucleotide is complementary to at least a portion of the single stranded DNA, and wherein the single stranded DNA is retained within the chamber by the filtration membrane;
   (b) providing a DNA polymerase and four deoxynucleotide triphosphates (dNTPs) comprising dATP, dGTP, dCTP, and dTTP, wherein each dNTP is 3'-end labeled (cdNTP) with a cleavable tag that distinguishes it from the other deoxynucleotide triphosphates;
   (c) extending the single stranded DNA hybridized to the oligonucleotide by one complementary end-labeled cdNTP in a polymerase extension reaction, wherein the tag on the extended cdNTP blocks further extension by the DNA polymerase;
   (d) washing the cdNTPs that are not extended onto the single stranded DNA through the filtration membrane, wherein the filtration membrane allows cdNTPs to pass through the membrane and retains the single stranded DNA in the chamber;
   (e) cleaving the tag from the complementary cdNTP;
   (f) washing the cleaved tag through the filtration membrane; and
   (g) detecting the cleaved tag that is washed through the filtration membrane of step (f), thereby identifying the complementary dNTP.

2. The method of claim 1, further comprising the step of repeating steps (b) through (g) on the sample of single stranded DNA.

3. The method of claim 1, wherein the cleavable tags are cleavable by chemical cleavage.

4. The method of claim 3, wherein the cleavable tags are acid cleavable tags.

5. The method of claim 3, wherein the cleavable tags are base cleavable.

6. The method of claim 1, wherein the tags are photocleavable.

7. The method of claim 1, wherein the tag is a fluorescent tag.

8. The method of claim 1, wherein the tag is a mass tag.

9. A method of determining a nucleic acid sequence, comprising:
   (a) hybridizing a complementary oligonucleotide to a single stranded DNA, wherein the single stranded DNA is retained within a chamber by a filtration membrane that is attached to the chamber, wherein the single stranded DNA is not attached to the filtration membrane, wherein the complementary oligonucleotide is hybridized adjacent to a primer that is hybridized to the single stranded DNA, wherein the complementary oligonucleotide is 3'-end labeled with at least one cleavable tag that distinguishes it from other complementary oligonucleotides;
   (b) ligating the hybridized complementary oligonucleotide to the adjacent primer to generate a ligated complementary oligonucleotide;
   (c) cleaving the tag from the ligated complementary oligonucleotide;
   (d) washing the cleaved tag through the filtration membrane that allows the cleaved tag to pass through the membrane; and
   (e) detecting the cleaved tag that distinguishes the complementary oligonucleotide that is washed through the filtration membrane of step (e).

10. The method of claim 9, further comprising the step of repeating steps (a) through (e) on the single stranded DNA.

11. The method of claim 9, wherein one or more tags are cleaved by chemical cleavage.

12. The method of claim 11, wherein the cleavable tags are acid cleavable tags.

13. The method of claim 11, wherein the cleavable tags are base cleavable.

14. The method of claim 9, wherein the tags are photocleavable.

15. The method of claim 9, wherein the tag is a fluorescent tag.

16. The method of claim 9, wherein the tag is a mass tag.

* * * * *